US011986192B2

(12) United States Patent
Luedi (10) Patent No.: US 11,986,192 B2
(45) Date of Patent: May 21, 2024

(54) ULTRASONIC BONE CUTTING DEVICE WITH INTEGRATED SENSING (71) Applicant: Medtronic Xomed, Inc., Jacksonville, FL (US)

(72) Inventor: Manfred K. Luedi, Jacksonville, FL (US)

(73) Assignee: Medtronic Xomed, Inc., Jacksonville, FL (US)

(*) Notice: Subject to any disclaimer, the term of this patent is extended or adjusted under 35 U.S.C. 154(b) by 264 days.

(21) Appl. No.: 17/516,131

(22) Filed: Nov. 1, 2021

(65) Prior Publication Data
US 2022/0160373 A1 May 26, 2022

Related U.S. Application Data (60) Provisional application No. 63/118,531, filed on Nov. 25, 2020.

(51) Int. Cl.
*A61B 17/16* (2006.01)
*A61B 17/32* (2006.01)

(52) U.S. Cl.
CPC ...... *A61B 17/1628* (2013.01); *A61B 17/1615* (2013.01); *A61B 17/1626* (2013.01); *A61B 17/320016* (2013.01); *A61B 17/1695* (2013.01); *A61B 2017/320044* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1662; A61B 17/1671; A61B 17/32; A61B 17/320016; A61B 17/320068;
(Continued)

(56) References Cited

U.S. PATENT DOCUMENTS

| 5,026,387 A | 6/1991 | Thomas |
| 6,579,244 B2 | 6/2003 | Goodwin |
| 9,554,807 B2 | 1/2017 | McGinley et al. |

(Continued)

FOREIGN PATENT DOCUMENTS

| CN | 111281479 | 6/2020 |
| DE | 102010014148 | 10/2011 |

(Continued)

OTHER PUBLICATIONS

Extended European Search Report from EP Application 21210176.0 dated Mar. 25, 2022, 6 pgs.

*Primary Examiner* — Eric S Gibson
(74) *Attorney, Agent, or Firm* — Husch Blackwell LLP (57) ABSTRACT Surgical instruments with ultrasonic cutting and sensing capabilities, as well as related systems and methods, are disclosed herein. In one aspect, the present disclosure provides a surgical instrument including a housing; an ultrasonic transducer contained in the housing and capable of acting as an ultrasonic receiver; an output member at least partially received in the housing and configured to be driven by the ultrasonic transducer; a dissection head having an attachment portion configured to be selectively driven by the ultrasonic transducer; and a controller operable to initiate and stop the ultrasonic transducer according to an alternating duty cycle.

19 Claims, 7 Drawing Sheets (58) Field of Classification Search
CPC .......... A61B 2017/00106; A61B 2017/00146; A61B 2017/320069
See application file for complete search history.

(56) References Cited

U.S. PATENT DOCUMENTS

| | | | |
|---|---|---|---|
| 9,561,544 B2* | 2/2017 | Walsh | A61B 17/1695 |
| 9,788,851 B2* | 10/2017 | Dannaher | A61B 17/320092 |
| 9,855,060 B2 | 1/2018 | Ardel et al. | |
| 9,936,961 B2* | 4/2018 | Chien | A61B 17/1626 |
| 10,194,966 B2* | 2/2019 | Corpa de la Fuente | A61B 17/8811 |
| 10,390,895 B2* | 8/2019 | Henderson | A61B 17/320068 |
| 10,531,929 B2* | 1/2020 | Widenhouse | A61B 34/30 |
| 10,588,645 B1* | 3/2020 | Cao | A61B 17/164 |
| 2004/0058636 A1 | 3/2004 | Hinsch et al. | |
| 2013/0282038 A1* | 10/2013 | Dannaher | A61B 17/320068 606/1 |
| 2014/0239600 A1* | 8/2014 | Walsh | A61B 17/1624 279/141 |
| 2015/0342618 A1* | 12/2015 | Nguyen | A61C 8/0092 433/27 |
| 2016/0066972 A1* | 3/2016 | Corpa de la Fuente | A61B 17/8847 606/92 |
| 2018/0049820 A1* | 2/2018 | Widenhouse | A61B 34/37 |
| 2018/0049822 A1* | 2/2018 | Henderson | A61B 34/76 |
| 2022/0160373 A1* | 5/2022 | Luedi | A61B 17/16 |
| 2022/0218421 A1* | 7/2022 | Junio | A61B 17/1626 |

FOREIGN PATENT DOCUMENTS

| | | | | |
|---|---|---|---|---|
| EP | 4005509 A1 * | 6/2022 | ......... | A61B 17/1615 |
| WO | WO-2013029039 A1 * | 2/2013 | ......... | A61B 17/1624 |
| WO | WO-2016037066 A1 * | 3/2016 | ......... | A61B 17/1626 |

* cited by examiner

ULTRASONIC BONE CUTTING DEVICE WITH INTEGRATED SENSING

RELATED APPLICATION

This application claims the benefit of U.S. Provisional Application No. 63/118,531 filed Nov. 25, 2020, which is hereby fully incorporated herein by reference.

FIELD

The present disclosure generally relates to surgical instruments for use in the dissection of bone and other tissue. More particularly, the present disclosure relates to a surgical instrument with ultrasonic cutting and sensing capabilities.

BACKGROUND

In various surgical procedures, it is necessary to dissect bone or other tissue. Many conventional surgical instruments used for the dissection of bone or other tissue employ pneumatic or electrical motors to rotate a cutting element. In their most basic form, these surgical instruments comprise a motor portion having a rotary shaft, a dissection tool having a cutting or abrading element that is moved by the rotating shaft of the motor, and a coupling arrangement for connecting the dissection tool to a spindle or collet of the rotary shaft. The spindle or collet of the rotary shaft is usually housed within a base that is attached to the motor.

Bone cutting or drilling is performed in many surgical procedures in orthopedic surgery as well as in the fields of neurosurgery, plastic surgery, and otorhinolaryngology. For example, in surgery to fixate fractured bones after a trauma, implants like nails, plates, screws, and wire are used and these implants are inserted into holes made by drilling cylindrical tunnels into the bone. Risks during the drilling procedure, include harm caused to the bone, muscle, nerves, and venous tissues by the high temperatures which can be generated by the high-speed rotation of the drill bit, if the rapidly rotating drill is wrapped by the surrounding tissue in an uncontrolled manner, or if the drill bit does not stop immediately after it exits the second cortex of the bone.

With the increasing demand for the development of minimally invasive techniques, the difficulty of achieving satisfactory safety and accuracy of procedures is increasing day by day. For example, spinal surgery is complicated by intertwined nerve tissue, making even minor mistakes extremely dangerous, with a high risk of soft tissue and nerve damage that can have far-reaching and life-changing effects. At present, surgeons mostly adopt medical instruments such as rongeurs, micro saws, high-speed grinding heads and the like to cut bone tissues, but the amount of bleeding can be substantial. Bone tissues are easy to damage themselves, as well as being surrounded by delicate soft tissue.

The use of an ultrasonic cutting instrument as a novel bone removal instrument has a number of advantages over conventional bone removal tools, including tissue selectivity, anti-roll-scraping properties, cold cutting, ease of operation, blood supply protection, and reduced procedure time.

However, ultrasonic cutting tools still present safety issues during the surgical procedure. In surgery, tissue density and elasticity properties can vary and soft tissue avoids certain cutting risks due to partial absorption of high-frequency impact energy. For example, in spinal surgery, the yellow ligament and dura-mater are easily cut after the vertebral plate is cut in clinical operation. Spinal soft tissue damage can lead to multiple risks and complications such as dural rupture, cerebrospinal fluid leakage, and iatrogenic nerve injury.

Thus, there exists a present need in the art for improved surgical aids to minimize unintended off-target tissue damage. There exists a further need in the art for improved surgical tools to assist surgeons in navigating the low-visibility conditions of minimally invasive surgeries.

SUMMARY

The techniques of this disclosure generally relate to surgical instrument with ultrasonic cutting and sensing capabilities, as well as related systems and methods.

In one aspect, the present disclosure provides a surgical instrument comprising a housing; an ultrasonic transducer contained in the housing and capable of acting as an ultrasonic receiver; an output member at least partially received in the housing and configured to be driven by the ultrasonic transducer; a dissection head having an attachment portion configured to be selectively driven by the ultrasonic transducer; and a controller operable to initiate and stop the ultrasonic transducer according to an alternating duty cycle.

In another aspect, the disclosure provides a system for combined ultrasonic cutting and sensing, comprising an ultrasound transducer; a memory containing an alternating duty cycle algorithm for alternating cutting and sensing frequencies; a processor, configured to operate the ultrasound transducer and execute instructions stored in the memory such that the ultrasound transducer operates at a first frequency, the first frequency associated with a cutting function and alternates, according to the alternating duty cycle, such that the ultrasound transducer stops operating at the first frequency and operates at a second frequency, the second frequency associated with ultrasonic sensing.

In yet another aspect, a method for operating a combined ultrasonic cutting and sensing device comprises initiating an ultrasonic transducer; and operating the ultrasonic transducer according to an alternating duty cycle such that the ultrasonic transducer operates at a first frequency associated with a cutting function and also alternately operates at a second frequency associated with a sensing function.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The disclosure can be more completely understood in consideration of the following detailed description of various embodiments of the disclosure, in connection with the accompanying drawings, in which.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

The following description of various embodiments is merely exemplary in nature and is in no way intended to limit the invention, its application, or uses.

Real-time detection of bone-nerve or bone-tissue boundaries while dissecting bone during a surgical procedure can provide additional safety for protecting critical patient anatomy and providing better surgical outcomes.

Embodiments of the present disclosure use an ultrasonic bone cutting device and can drive the device in two different, time-interlaced modalities. A first cutting modality uses ultrasonic vibration to resect or dissect bone, using a specific amplitude and frequency. In a second sensing modality, an actuator sends out one or more pulses and acts as a sensor, listening for audio wave reflections from boundaries to calculate a distance of the cutting tip from next boundary, providing guidance using a simplified version of ultrasonic imaging.

The drive algorithm can run an optimized duty cycle to switch the actuator back and forth between cutting and sensing modes to get several measurements per second and can automatically stop when the tip is at a pre-defined distance from a detected boundary.

Applications of ultrasonic technology can be broadly grouped into two categories: sensing, and actuation. Sensing applications typically require both pulse transmission and reception. In contrast, cutting applications typically require the continuous or semi-continuous generation of high-power ultrasonic vibration. Disclosed herein is an integration of sensing and cutting applications, to facilitate more efficient sensing of tissues and tissue boundaries immediately adjacent to the cutting surface of an ultrasonic cutting tool. Using the bone removal tip to also sense remaining depth to next boundary provides a built-in safety feature to protect sensitive patient anatomy. Devices and systems according to the present disclosure can be used stand-alone, such as a handheld device operated by a surgeon, or may be coupled with surgical navigation, with features according to the present disclosure increasing cutting accuracy and reduce the likelihood of soft tissue structure damage. For example, in the context of a spinal operation, it can reduce the occurrence rate of vertebral body breach. In other contexts, such as trepanning in skull procedures, it can reduce the risk of breach into the brain space.

Figure 1:
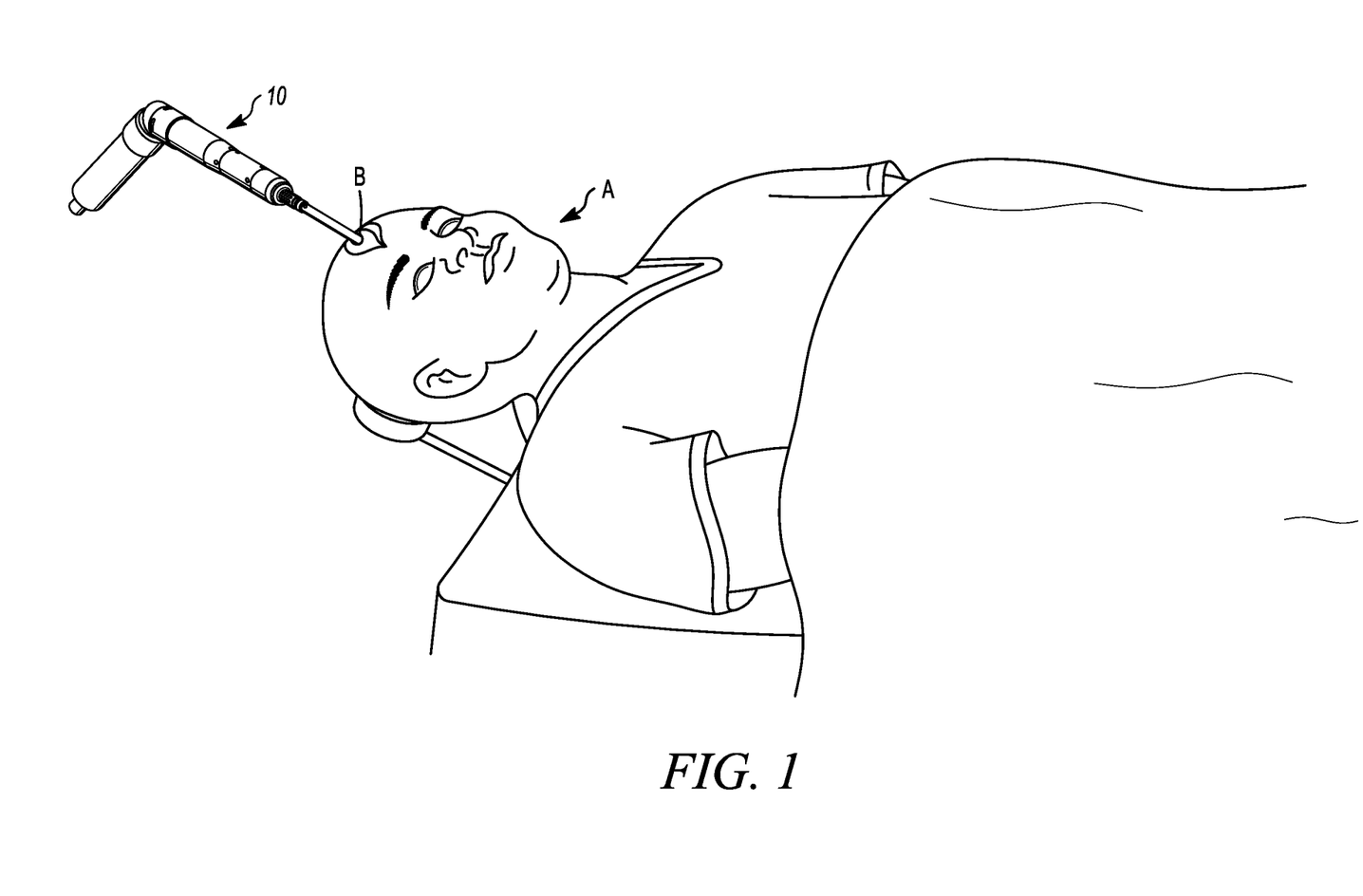
FIG. 1 is an illustration of a surgical dissection tool according to the present disclosure used in a human patient, according to embodiments of the present disclosure.
Figure 2A:
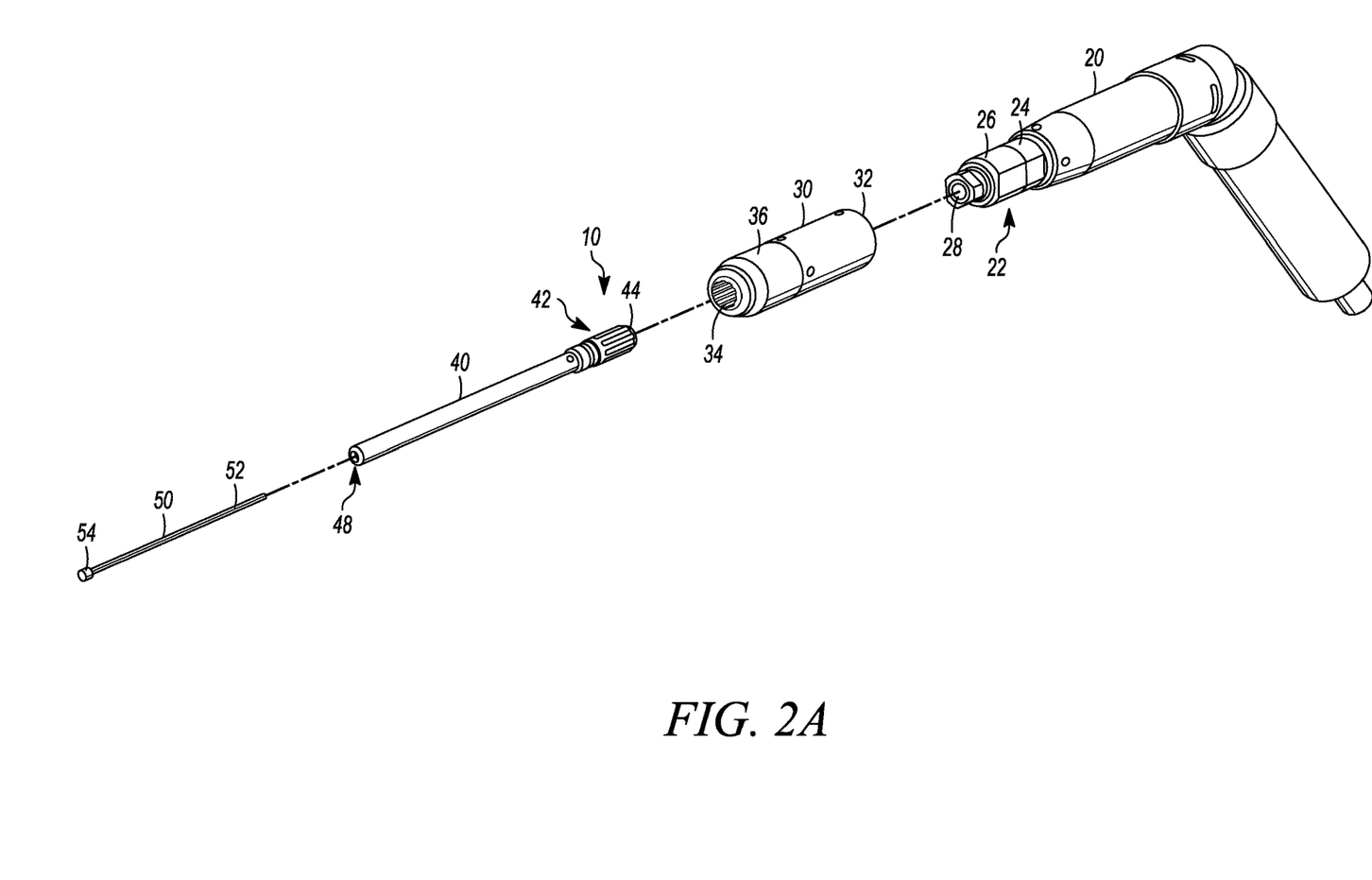
FIG. 2A is a partially exploded perspective view of an embodiment of a surgical dissection tool, according to embodiments of the present disclosure.
Figure 2B:
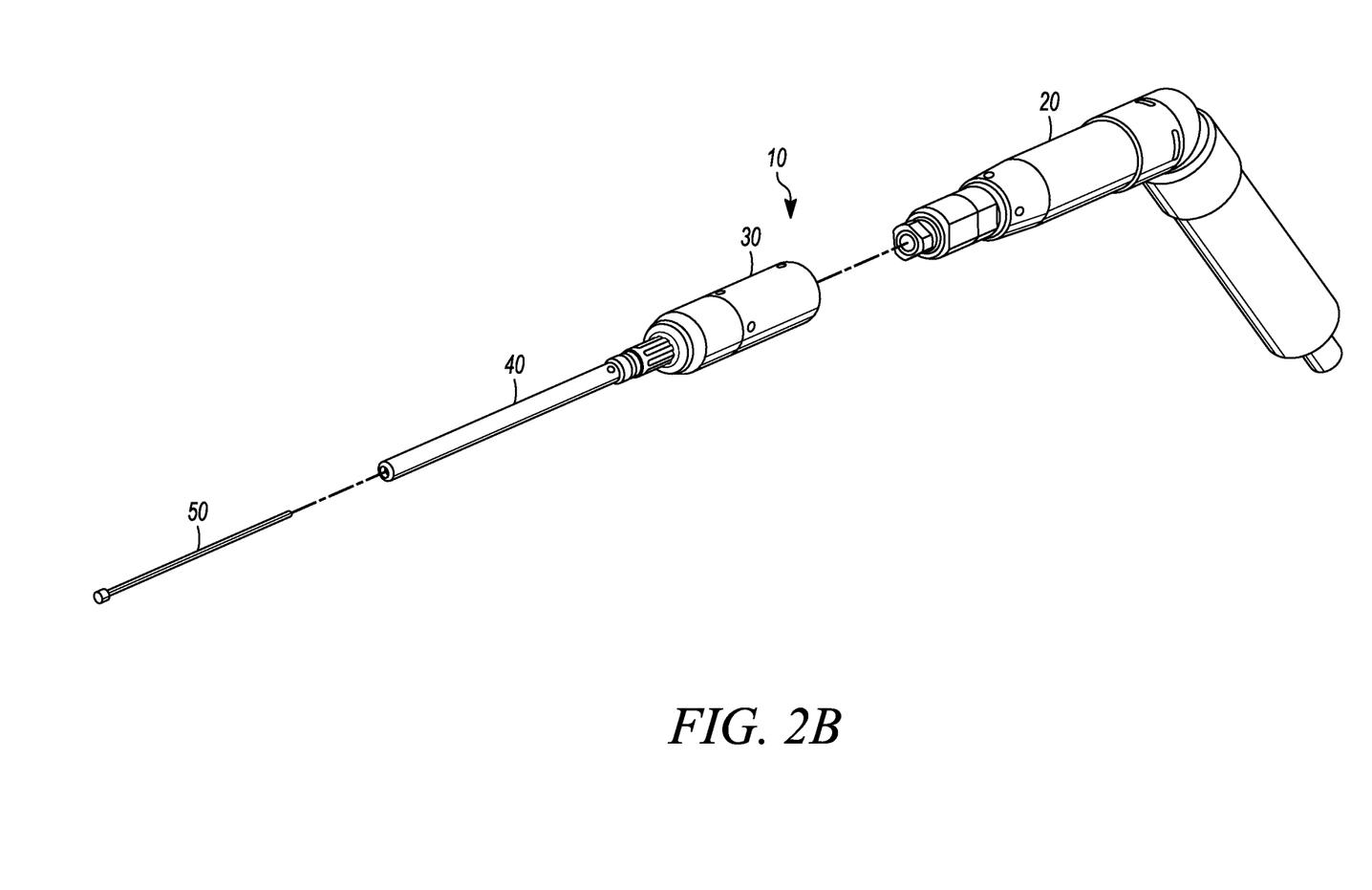
FIG. 2B is a partially exploded perspective view of the embodiment of FIG. 2A, according to embodiments of the present disclosure.
Figure 2C:
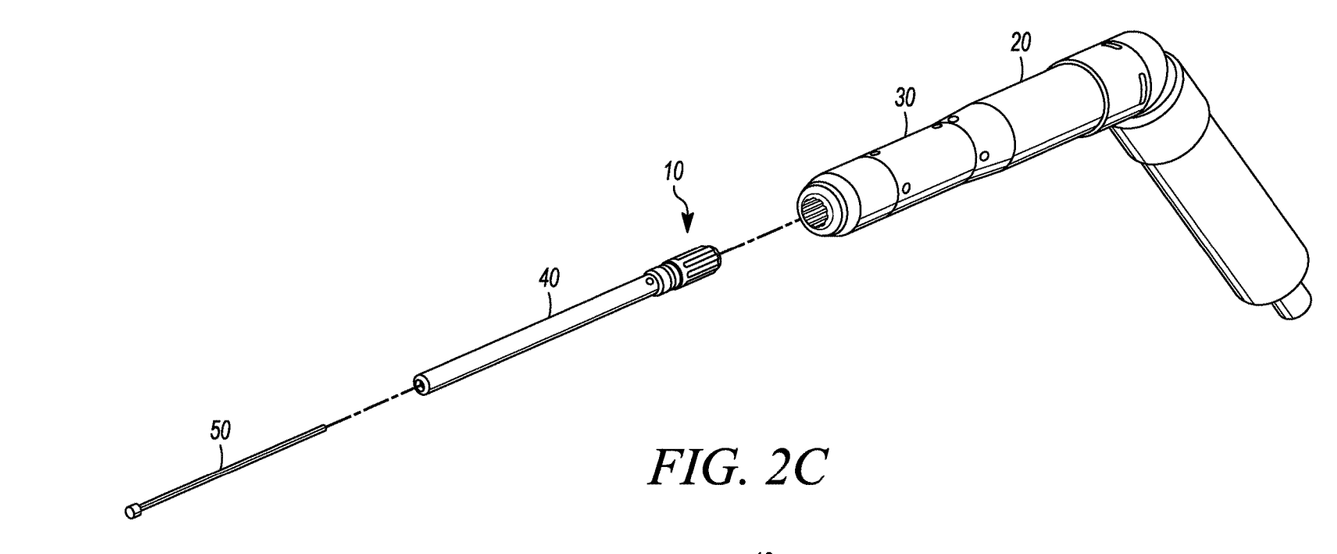
FIG. 2C is a partially exploded perspective view of the embodiment of FIG. 2A, according to embodiments of the present disclosure.
Figure 2D:
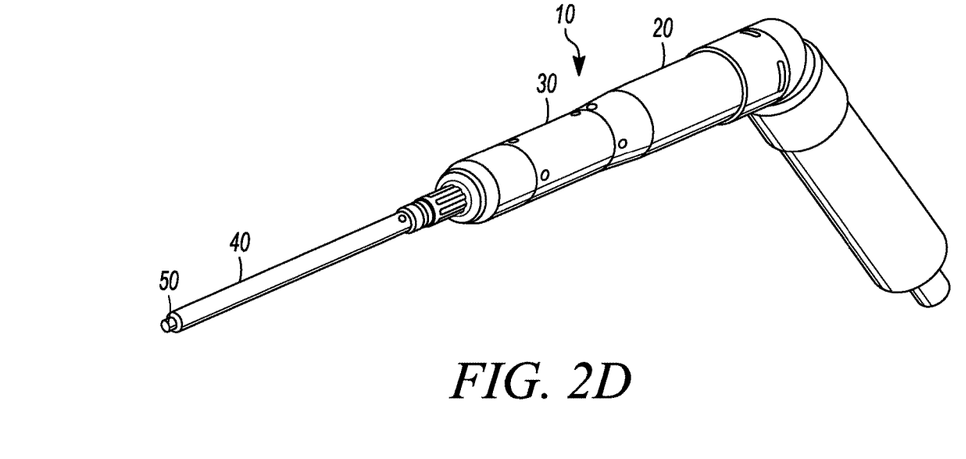
FIG. 2D is an assembled perspective view of the embodiment of FIG. 2A, according to embodiments of the present disclosure.

Referring now to FIG. 1, shown is a human patient A undergoing a neurological operation. As is common practice, access to the brain or other neurological structures often requires delicate dissection of bone and other tissues B to gain access. By way of example, dissection tool assembly 10 in accordance with one aspect of the present disclosure is shown being utilized to dissect a portion of patient A's bone and other tissue B adjacent to the surgical access site.

Referring now to FIGS. 2A through 2D, an example dissection tool assembly 10 for the dissection of bone or other tissue is illustrated. A pneumatic motor 20 is illustrated having a collet assembly 22 disposed on its distal end. Collet assembly 22 can include a proximal movable portion 24 and a distal fixed portion 26. A shaft receiving aperture 28 on the distal end can slidably receive a rotary shaft. The dissection tool assembly 10 may further include an attachment base coupling assembly 30 adapted to be received about collet assembly 22 and having an attachment aperture 34 at its distal length. An attachment tube 40 can be provided having a proximal portion 42 with grooves 44 extending along a portion thereof. The distal end of attachment tube 40 can include a tool receiving aperture 48. Coupling assembly 30 and attachment tube 40 can be combined to form a telescoping attachment assembly 12. An exemplary illustration of a dissection tool 50 is also shown. Dissection tool 50 can include an elongated shaft 52 and a tissue dissection head 54.

In embodiments, the device may be a handheld device or fully or partially machine-operated or robotic.

Pneumatic motor 20 may be excluded in embodiments, with an ultrasonic transducer used as a driver instead. Various ultrasonic transducers are envisioned, including but not limited to a bolt clamped Langevin transducer or other piezoelectric transducer.

Figure 3A:
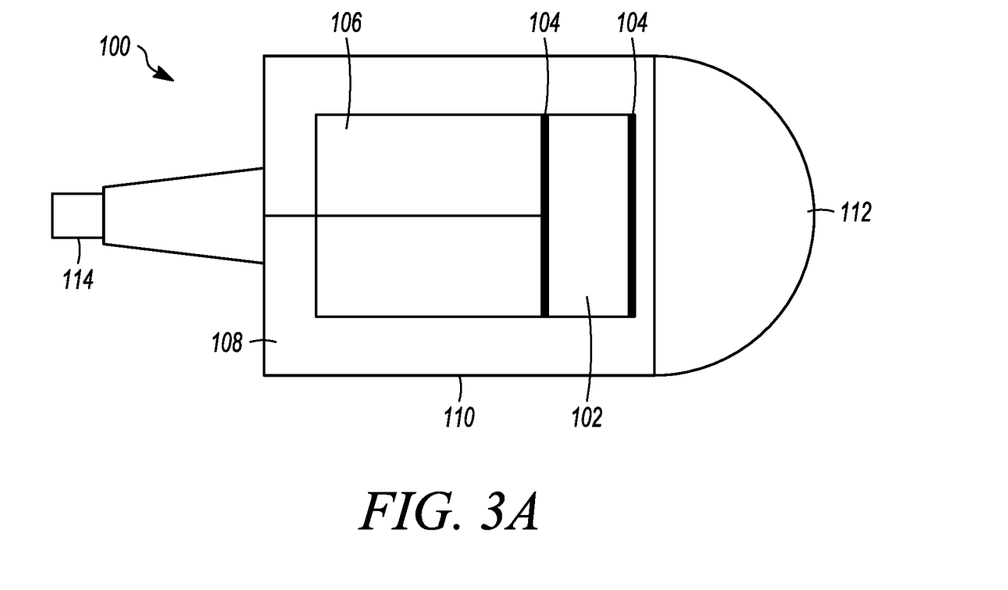
FIG. 3A is an example ultrasonic transducer, according to embodiments of the present disclosure.

As an example, a common arrangement for a sensing transducer 100 is shown in FIG. 3A. Sensing transducer 100 can comprise a piezoelectric element 102, electrodes 104, damping body 106, sound insulation 108, casing or body 110, transformation layer 112, and electrical supply 114.

Electrical supply 114 provides an alternating current to electrodes 104, producing a potential difference across piezoelectric element 102. The potential causes ultrasonic vibration of the piezoelectric element 102 which are transmitted through the transformation layer 112. Vibrations, or sound waves, rebounding off materials may be received through transformation layer 112 and received by piezoelectric element.

Damping body 106 primarily serves to reduce vibrations of piezoelectric element 102 during transmission. Sound insulation 108 can provide for direction of the vibrations generated by piezoelectric element 102 through the transformation layer 112, rather than throughout the transducer 100. Casing or body 110 can provide for containment of the elements of the transducer and other portions of the cutting/sensing tool as well as handling of the tool.

Figure 3B:
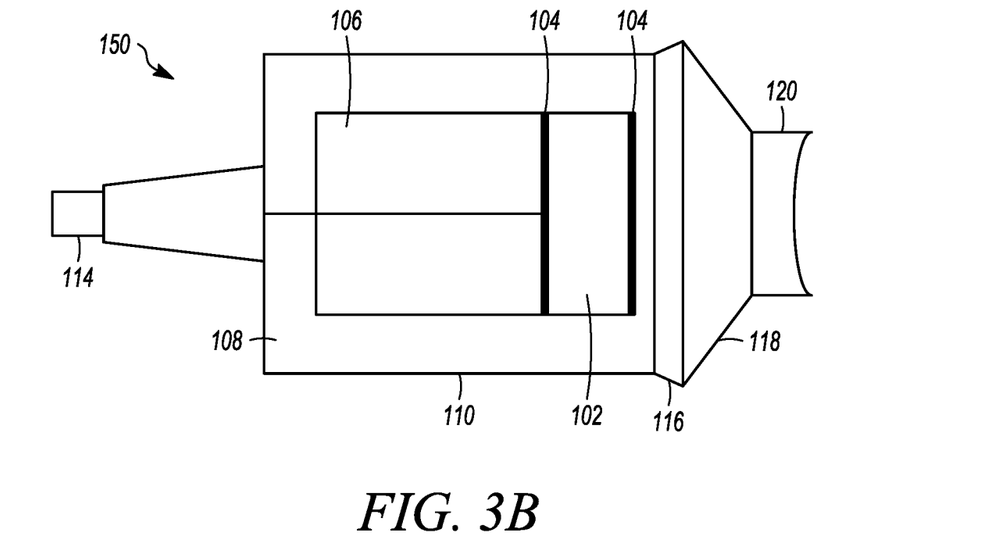
FIG. 3B is another example ultrasonic transducer, according to embodiments of the present disclosure.

FIG. 3B depicts an example transducer 150 with a cutting or dissection head 120, according to embodiments of the present disclosure. Transducer 150 may comprise the piezoelectric element 102, electrodes 104, damping body 106, sound insulation 108, casing or body 110, and electrical supply 114. In embodiments, collet 116, coupling assembly 118, and dissection head may be substantially similar to collet 22, couple assembly 30 and dissection head 54 of FIGS. 2A-2D.

In embodiments, a transformation layer, such as transformation layer 112, may be internal to other components which serve to target vibrations generated by piezoelectric element 102. For example, collect 116 may contain a transformation layer.

In embodiments, an ultrasonic transducer that is able to act as a receiver can be used, to allow a single actuator to be used for the both cutting and sensing functions. In embodiments, separate transducers can instead be used, such as a first transducer optimized for driving the dissection head and a second transducer optimized for sensing. These separate transducers can be arranged in a variety of ways. In one embodiment, the arrangement can be serial, with one transducer stacked on top of another and each driven alternately. In other embodiments, the arrangement can be parallel, or some combination of serial and parallel arrangements can be used.

In embodiments, a controller may be associated with electrical supply 114, and control the supplied alternating current according to an alternating duty cycle. The duty cycle can be optimized to alternate between a desired cutting frequency, and amplitude, and a sensing frequency and amplitude. In embodiments, the controller may be configured such that the sensing function operates multiple times per second.

In embodiments, a single transducer may be configured with a controller which changes the applied alternating current to achieve different output frequencies from the transducer.

In embodiments, a device can comprise multiple transducers. A first transducer may be optimized for a cutting frequency and a second transducer may be optimized for a sensing frequency. The first and the second transducer may have alternating duty cycles such that the second transducer is "on" when the first transducer is "off."

For example, a 60% duty cycle indicates the signal is on 60% of the time but off 40% of the time. The "on time" for a 60% duty cycle can be a fraction of a second, a day, or even a week, depending on the length of the period. Thus, various duty cycles are possible which provide for frequent sensing by a device according to the present disclosure. If the first transducer has a 60% duty cycle as discussed, the second transducer may have a 40% duty cycle offset such that the "on time" of the second transducer occurs during the "off time" of the first transducer.

Figure 4:
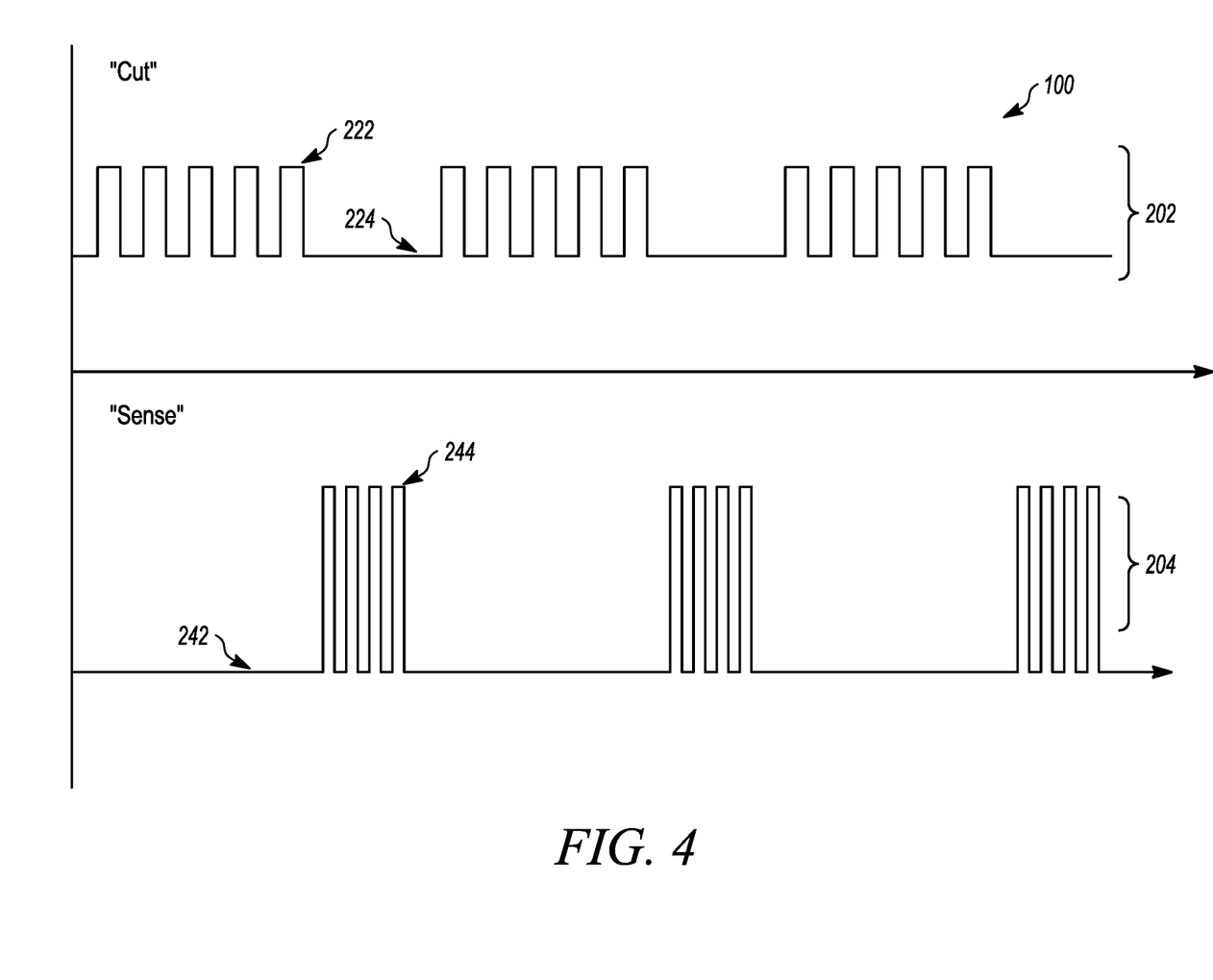
FIG. 4 is a graph of an example alternating duty cycle for operation of an ultrasonic transducer, according to embodiments of the present disclosure.

As another example, referring now to FIG. 4, a graph 200 of an example duty cycle is shown. An alternating duty cycle may generally favor cutting (e.g., allot a greater percentage of time in a given cycle to a cutting frequency) as cutting is likely to take more time than sensing in many applications. Depending on sensing efficiency, in embodiments only 5% of a cycle time may be dedicated to sensing, leaving 95% to cutting, increasing the bone removal rate. In embodiments the ratio between cutting and sensing can vary considerably depending on the application or be selectable by the user depending on anatomical risk, e.g., 100% cut in no or low risk areas, 50-50 for high-risk areas, etc. In embodiments adjustment of the device duty cycle may be automatic, for example when used in conjunction with navigation or navigation pre-surgery planning. For instance, a surgeon or other user can identify critical structures according to the navigation and adjust the active-duty cycle ratio accordingly.

In example graph 200, the alternating duty cycle is depicted as a first duty cycle 202 and a second, offset, duty cycle 204. First duty cycle 202 is, for example, a "cutting" cycle and may generally represent a transducer operating at a cutting frequency. For example, for cutting bone or other mineralized tissue, the frequency may be within a range of 20-40 kHz. Second duty cycle 204 is, for example, a sensing cycle and may generally represent a transducer operating at a sensing frequency (e.g., between about 40 kHz and about 250 kHz) and, in embodiments, may further represent a transducer also acting as an ultrasonic receiver.

In an example application using a 95% duty cycle for the cutting frequency, a 5% duty cycle may then be used for the sensing frequency. The two duty cycles can be offset such that when the first duty cycle 202 is active, area 222, the second duty cycle 204 can be inactive, area 242. Similarly, when the second duty cycle 204 is active, area 244, the first duty cycle 202 can be inactive, area 224. The two duty cycles 202, 204 can be interlocked, such that if an obstacle or obstruction is detected during a sensing cycle, e.g., area 244, an integrated controller can be configured to prevent the cutting cycle and frequency from engaging without user acknowledgment or intentional activation. Such integration between the cutting and sensing function may assist in ensuring cutting does not proceed without a high degree of confidence that cuts are made in the desired tissue. For example, the sensing feature can be configured to stop the engagement of the cutting operation based on a detected change in density, the detection of an obstruction or tissue-type not expected based on pre-surgery planning and navigation, disagreement between what is detected by the integral sensor of the ultrasonic cutting device and a secondary imaging or navigation sensor, etc.

The offset between the duty cycles dedicated for each of the cutting and sensing frequencies can prevent interference between cutting and sensing frequencies and, in embodiments, may aide in the use of a single transducer for both functions. In embodiments, the duty cycle may be set to generally favor cutting for increased efficiency, while the period may be set so that despite cutting dominating any given cycle, the device is still configured to execute a sensing operation one or more times per second.

The above description has been directed to a coupling assembly 30 that is detachable from motor 20, however; it is contemplated and hereby disclosed that coupler 30 may be integrated with motor 20 in a substantially integral unit. Still further, attachment tube 40 and dissection tool 50 have been shown as substantially straight components. It will be appreciated and is hereby disclosed that attachment tube 40 may be curved to accommodate various applications. It being understood that dissection tool 50 may have sufficient flexibility to conform to the curvature of the attachment along its length.

Figure 5:
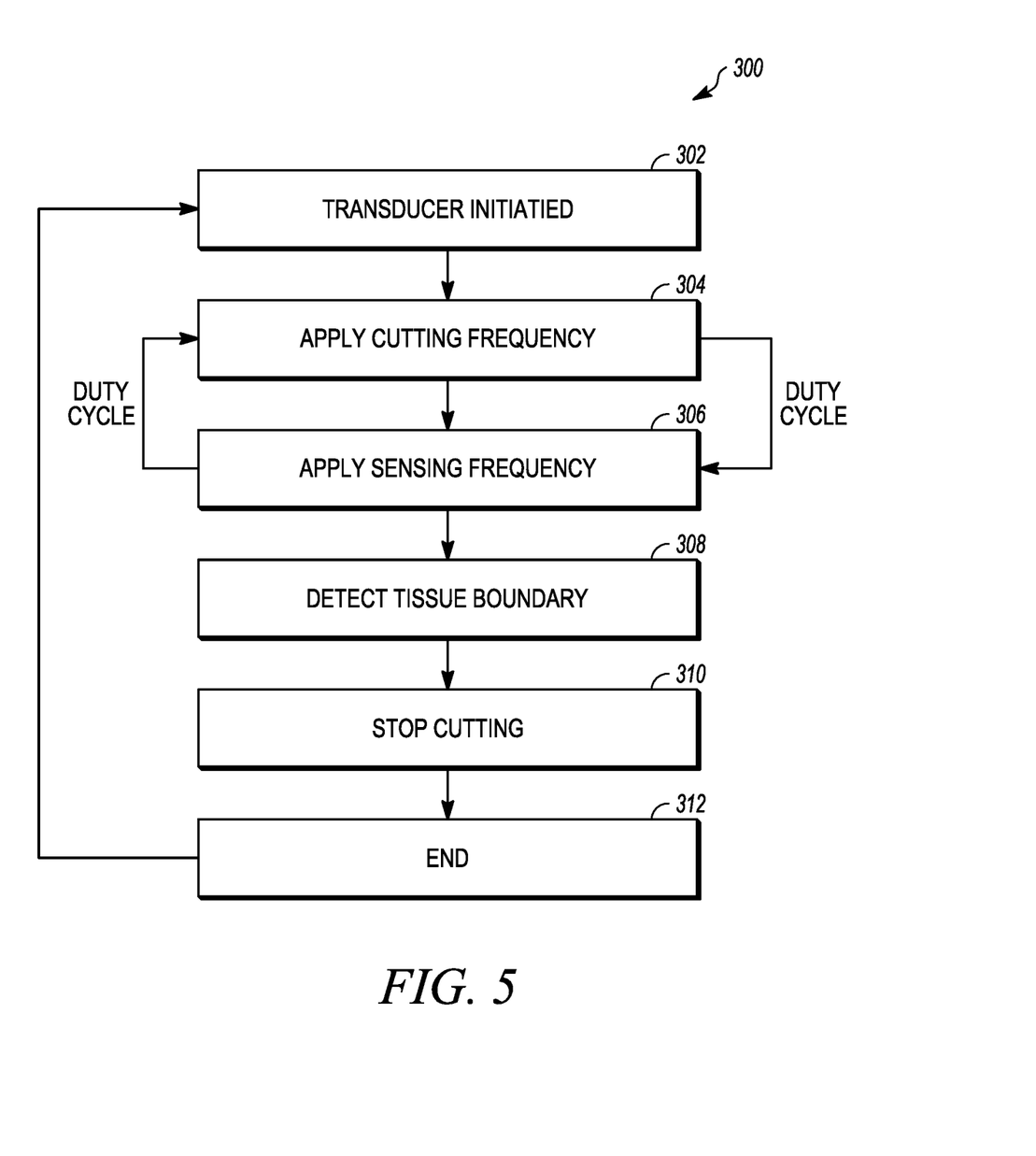
FIG. 5 is a flowchart of an example method for operation of an ultrasonic cutting and sensing device, according to embodiments of the present disclosure.

Referring now to FIG. 5, an example method 300 is shown for use of an ultrasonic cutting and sensing tool according to embodiments of the present disclosure.

In use, an operator, such as a surgeon or a surgical system or robot, can apply a device according to the present disclosure to a tissue to be dissected, such as a bone. The ultrasonic transducer of the device can be initiated, as at operation 302, such as by applying an alternating current.

The transducer can be initiated at a first frequency, such as a cutting frequency, as at operation 304, and automatically shift to a second frequency, such as a sensing frequency, as at operation 306, according to a duty cycle. The duty cycle may be controlled by a controller, such as a processor according to an algorithm, such as by changing the applied alternating current to achieve different frequencies.

The sensing frequency can be configured for typical imaging output or may be otherwise configured to assist in the operation. For example, sensing output may be configured to detect changes in the tissue at the cutting edge of the tool, for example a change in density or other characteristic of the tissue, in order to determine a tissue boundary, as at operation 308.

By alternating the output frequency in this way, sensing is achieved directly at the point where cutting is occurring. Thus, if the cutting edge of a device according to the present disclosure is at a tissue boundary, it may be detected even if such a boundary is not readily visible via imaging. Further, the detection may be configured to trigger an automatic stop of cutting operations by the tool, such as operation 310, when a tissue boundary is detected. Surgeons and other operators may proceed in low-visibility and high-risk areas with greater confidence and efficiency by being able to rely on their cutting tool to stop at any tissue boundary to allow the surgeon to reassess whether continuing to cut is desirable. Once a "stop" signal is received, such as at operation 310, the system or controller may end the operation or cycle, such as at operation 312. In embodiments, disengaging the transducer in this way may further aide in device safety by ensuring that cutting operations cannot be initiated without user awareness or acknowledgment that an obstacle, such as a tissue boundary, has been detected. When a surgeon or other user has verified that safe conditions for cutting have been restored or otherwise exist, the transducer can be initiated, as at operation 302.

The above-described embodiments of the present disclosure may be assembled and adjusted by manual manipulation of the outer surfaces of the components. It will be understood that in this preferred configuration, it is advantageous for the user such that additional instrumentation, tools or intricate movements are not required to accommodate the coupling and adjustment of the various components.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques can be fully implemented in one or more circuits or logic elements.

What is claimed is:

1. A surgical instrument, comprising:
   a housing;
   an ultrasonic transducer contained in the housing and capable of acting as an ultrasonic receiver, wherein the ultrasonic transducer is a first ultrasonic transducer optimized for cutting and the surgical instrument further comprises a second ultrasonic transducer, separate from the first ultrasonic transducer optimized for sensing;
   an output member at least partially received in the housing and configured to be driven by the ultrasonic transducer;
   a dissection head having an attachment portion configured to be selectively driven by the ultrasonic transducer; and
   a controller operable to initiate and stop the first ultrasonic transducer and the second ultrasonic transducer according to an alternating duty cycle.

2. The surgical instrument of claim 1, wherein the ultrasonic transducer operates alternatively at a cutting frequency and a sensing frequency according to the alternating duty cycle.

3. The surgical instrument of claim 1, wherein the alternating duty cycle comprises a first duty cycle, associated with the first transducer, offset with a second duty cycle, associated with the second transducer.

4. The surgical instrument of claim 1, wherein the alternating duty cycle comprises a first duty cycle offset with a second duty cycle.

5. The surgical instrument of claim 4, wherein the first duty cycle and the second duty cycle have the same period.

6. The surgical instrument of claim 5, wherein the first duty cycle is associated with a first frequency and the second duty cycle is associated with a second frequency.

7. The surgical instrument of claim 6, wherein the first duty cycle is offset with the second duty cycle such that when the ultrasonic transducer operates at the first frequency according to the first duty cycle, the second duty cycle is in an inactive period, and wherein when the ultrasonic transducer operates at the second frequency according to the second duty cycle, the first duty cycle is in an inactive period.

8. The surgical instrument of claim 6, wherein the first frequency is associated with a cutting function.

9. The surgical instrument of claim 8, wherein the first frequency is between 20 kHz and 40 kHz.

10. The surgical instrument of claim 4, wherein the first duty cycle is 95% and the second duty cycle is 5%.

11. The surgical instrument of claim 4, wherein the first duty cycle is 50% and the second duty cycle is 50%.

12. The surgical instrument of claim 4, wherein the first duty cycle and the second duty cycle are complementary.

13. The surgical instrument of claim 12, wherein the alternating duty cycle is adjustable, such that as the first duty cycle is changed and the second duty cycle exhibits an inverse change.

14. The surgical instrument of claim 1, wherein the ultrasonic transducer, when operating at a sensing frequency and acting as the ultrasonic receiver, senses a tissue boundary in proximity to the dissection head.

15. The surgical instrument of claim 14, wherein the controller automatically stops the ultrasonic transducer in response to detecting the tissue boundary.

16. The surgical instrument of claim 14, wherein the tissue boundary is detected as a change in density.

17. A system for combined ultrasonic cutting and sensing, comprising:
- an ultrasound transducer;
- a memory containing an alternating duty cycle algorithm for alternating frequencies; and
- a processor, configured to operate the ultrasound transducer and execute instructions stored in the memory such that:
  - the ultrasound transducer is a first ultrasonic transducer optimized for cutting that operates at a first frequency, the first frequency associated with a cutting function, and alternates, according to the alternating duty cycle algorithm, such that the ultrasound transducer stops operating at the first frequency and, after at least a period of time, operates a second ultrasonic transducer, separate from the first ultrasonic transducer, optimized for sensing at a second frequency, the second frequency associated with ultrasonic sensing.

18. The system for combined ultrasonic cutting and sensing of claim 17, further comprising a dissection head selectively driven by the ultrasound transducer when the ultrasound transducer operates at the first frequency.

19. A method for operating a combined ultrasonic cutting and sensing device, comprising:
- initiating an ultrasonic transducer; and
- operating the ultrasonic transducer according to an alternating duty cycle such that the ultrasonic transducer is a first ultrasonic transducer optimized for cutting that operates at a first frequency, the first frequency associated with a cutting function, and alternates, after at least a period of time, according to the alternating duty cycle, such that the ultrasonic transducer stops operating at the first frequency and operates a second ultrasonic transducer, separate from the first ultrasonic transducer, optimized for sensing at a second frequency, the second frequency associated with ultrasonic sensing.

\* \* \* \* \*